United States Patent
Yasui et al.

(10) Patent No.: US 6,816,774 B2
(45) Date of Patent: Nov. 9, 2004

(54) $O_2$ SENSOR, APPARATUS FOR AND METHOD OF CONTROLLING AIR-FUEL RATIO, AND RECORDING MEDIUM STORING AIR-FUEL RATIO CONTROL PROGRAM

(75) Inventors: Yuji Yasui, Wako (JP); Yoshihisa Iwaki, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/366,354

(22) Filed: Feb. 14, 2003

(65) Prior Publication Data
US 2003/0154708 A1 Aug. 21, 2003

(30) Foreign Application Priority Data
Feb. 15, 2002 (JP) .......................... 2002-039174

(51) Int. Cl.[7] ............................................... B60T 7/12
(52) U.S. Cl. ...................... 701/108; 60/276; 60/285; 123/697; 701/115; 701/109
(58) Field of Search .......................... 701/108, 109, 701/115; 50/274, 275, 277, 276; 123/697; 60/285

(56) References Cited

U.S. PATENT DOCUMENTS

| | | | | |
|---|---|---|---|---|
| 5,485,382 A | * | 1/1996 | Seki et al. .................. | 701/109 |
| 5,626,014 A | * | 5/1997 | Hepburn et al. .............. | 60/274 |
| 5,732,552 A | * | 3/1998 | Matsumoto et al. .......... | 60/276 |
| 5,966,930 A | * | 10/1999 | Hatano et al. ................ | 60/276 |
| 6,003,308 A | * | 12/1999 | Tsutsumi et al. ............. | 60/276 |
| 6,082,101 A | * | 7/2000 | Manaka et al. ............... | 60/285 |
| 6,151,547 A | * | 11/2000 | Kumar et al. ................ | 701/101 |
| 6,188,953 B1 | | 2/2001 | Yasui et al. ................. | 701/109 |
| 6,233,922 B1 | * | 5/2001 | Maloney ...................... | 60/276 |
| 6,308,697 B1 | * | 10/2001 | Surnilla et al. ............. | 123/672 |
| 6,354,269 B1 | * | 3/2002 | Saito et al. ................. | 123/436 |
| 6,502,389 B2 | * | 1/2003 | Katayama et al. ............ | 60/285 |
| 6,619,277 B2 | * | 9/2003 | Katoh ......................... | 123/672 |

FOREIGN PATENT DOCUMENTS

JP   11-324767   11/1999

* cited by examiner

Primary Examiner—Willis R. Wolfe
Assistant Examiner—Johnny H. Hoang
(74) Attorney, Agent, or Firm—Squire, Sanders & Dempsey L.L.P.

(57) ABSTRACT

A system controls the air-fuel ratio in an exhaust gas supplied from an internal combustion engine to a catalytic converter in order to keep an output voltage Vout of an $O_2$ sensor disposed downstream of the catalytic converter at a predetermined target value Vop. In the system, the temperature of an active element of the $O_2$ sensor is controlled at a predetermined temperature such that the output voltage of the $O_2$ sensor at an inflection point of output characteristics thereof is substantially the same as the target value Vop.

18 Claims, 3 Drawing Sheets

# O₂ SENSOR, APPARATUS FOR AND METHOD OF CONTROLLING AIR-FUEL RATIO, AND RECORDING MEDIUM STORING AIR-FUEL RATIO CONTROL PROGRAM

BACKGROUND OF THE INVENTION

1. Field of the Invention

The present invention relates to an $O_2$ sensor for use in the exhaust system of an internal combustion engine, an apparatus for and a method of controlling the air-fuel ratio in a system where an $O_2$ sensor is incorporated in the exhaust system of an internal combustion engine, and a recording medium which stores an air-fuel ratio control program for such a system.

2. Description of the Related Art

There has been proposed by the applicant of the present application a system for controlling the air-fuel ratio of an exhaust gas, i.e., the air-fuel ratio represented by the concentration of oxygen in an exhaust gas, supplied from an internal combustion engine to a catalytic converter for keeping the output voltage of an $O_2$ sensor disposed downstream of the catalytic converter at a predetermined target value (a constant value) in order to give a required exhaust gas purifying capability to the catalytic converter, which comprises a three-way catalyst or the like disposed in the exhaust system (passage) of the internal combustion engine (see, for example, Japanese laid-open patent publication No. 11-324767 and U.S. Pat. No. 6,188,953).

The proposed system is based on the phenomenon that when the air-fuel ratio of the exhaust gas supplied from the internal combustion engine to the catalytic converter is controlled at an air-fuel ratio state for settling the output voltage of the $O_2$ sensor disposed downstream of the catalytic converter at a predetermined constant value, the rates of purification of CO (carbon monoxide), HC (hydrocarbon), NOx (nitrogen oxide), etc. by the catalytic converter are kept well, i.e., substantially maximum, irrespective of the deteriorated state of the catalytic converter.

A further study made by the inventors of the present invention has revealed the following findings:

An $O_2$ sensor has its output characteristics changed when the temperature of an active element of the $O_2$ sensor, i.e., a sensitive element of the $O_2$ sensor which is held in contact with an exhaust gas, is changed by factors that affect the temperature of the active element of the $O_2$ sensor, such as the layout of the exhaust system of the internal combustion engine, the temperature of the exhaust gas, etc. A change in the output characteristics of the $O_2$ sensor tends to affect the control properties (control response and stability) of the air-fuel control process for keeping the output voltage of the $O_2$ sensor disposed downstream of the catalytic converter at a predetermined target value. This is because such a change in the output characteristics of the $O_2$ sensor varies the sensitivity of the output voltage of the $O_2$ sensor with respect to an air-fuel ratio change in the vicinity of the target value. The change in the output characteristics of the $O_2$ sensor also varies the value of the output voltage of the $O_2$ sensor disposed downstream of the catalytic converter for making well the exhaust gas purifying capability of the catalytic converter, i.e., the value of the output voltage of the $O_2$ sensor to be used as a target value for maintaining the good exhaust gas purifying capability of the catalytic converter.

Therefore, the control properties of the air-fuel control process for keeping the output voltage of the $O_2$ sensor at the target value may possibly be lowered depending on the temperature of the active element of the $O_2$ sensor or the operating conditions or environmental conditions of the internal combustion engine which affect the temperature of the active element of the $O_2$ sensor. Furthermore, if factors that affect the temperature of the $O_2$ sensor, e.g., the temperature of the exhaust gas, are likely to vary while the internal combustion engine is in operation, then it tends to be difficult to keep the desired exhaust gas purifying capability of the catalytic converter even when the output voltage of the $O_2$ sensor is controlled at the constant target value.

SUMMARY OF THE INVENTION

It is therefore an object of the present invention to provide an $O_2$ sensor having adequate output characteristics for maintaining the required exhaust gas purifying capability of a catalytic converter.

Another object of the present invention is to provide an apparatus for and a method of controlling an air-fuel ratio to reliably maintain the required exhaust gas purifying capability of a catalytic converter.

Still another object of the present invention is to provide a recording medium which stores a program for enabling a computer to control an air-fuel ratio to reliably maintain the required exhaust gas purifying capability of a catalytic converter.

Prior to describing the present invention in detail, the output characteristics of an $O_2$ sensor will first be described below. An $O_2$ sensor which is disposed in the exhaust passage of an internal combustion engine generates an output voltage depending on the concentration of oxygen in an exhaust gas which is brought into contact with an active element (sensitive element) of the $O_2$ sensor. The active element of the $O_2$ sensor is usually made of a material containing or coated with lead, silver, platinum, etc. (e.g., zirconia ($ZrO_2+Y_2O_3$)). The $O_2$ sensor has output characteristics (specifically, the characteristics of an output voltage of the $O_2$ sensor with respect to the air-fuel ratio in the exhaust gas which is represented by the concentration of oxygen sensed by the active element) generally referred to as a Z curve.

More specifically, as indicated by the solid-line curve "a" in FIG. 3 of the accompanying drawings, the output characteristics of the $O_2$ sensor have a segment e1 where the output voltage changes substantially linearly at a relative large gradient with respect to a change in the air-fuel ratio in the exhaust gas (hereinafter referred to as "large-gradient segment e1"), and segments e2, e3 where the gradient of a change in the output voltage with respect to a change in the air-fuel ratio is smaller than the large-gradient segment e1 (hereinafter referred to as "small-gradient segments e2, e3"). The small-gradient segments e2, e3 are present respectively on both sides of the large-gradient segment e1, i.e., respectively in regions that are richer and leaner than an air-fuel ratio range Δ corresponding to the large-gradient segment e1. The air-fuel ratio range Δ corresponding to the large-gradient segment e1 is a narrow range near a stoichiometric air-fuel ratio. The gradients of the small-gradient segments e2, e3 are much smaller than the gradient of the large-gradient segment e1. The small-gradient segments e2, e3 are joined to the large-gradient segment e1 by respective boundary segments e4, e5 that provide inflection points across which the gradient changes greatly. The output characteristics shown in FIG. 3 are general output characteristics of the $O_2$ sensor. The air-fuel ratio in the exhaust gas according to the above output characteristics, i.e., the air-fuel ratio represented by the concentration of oxygen that is sensed by the active element of the $O_2$ sensor, becomes richer, i.e., the ratio of fuel to air being larger, as the concentration of oxygen is lower, and becomes leaner, i.e., the ratio of fuel to air being smaller, as the concentration of oxygen is higher.

According to the inventors' knowledge, when the air-fuel ratio in the exhaust gas supplied to the catalytic converter is controlled to keep the output voltage of the $O_2$ sensor with the above output characteristics at a certain constant target value, it is preferable for the purpose of improving the control properties of such an air-fuel ratio control process to have the target value at a level substantially equal to an output voltage at the inflection point e4 at a richer air-fuel ratio, of the two inflection points e4, e5, or specifically to have the target value in an output voltage range in at the inflection point e4.

The above target value control is preferable for the following reasons: At the inflection point e4, the gradient (average gradient) of the output voltage of the $O_2$ sensor with respect to the air-fuel ratio is intermediate between the larger gradient of the large-gradient segment e1 and the smaller gradient of the small-gradient segment e2. Thus, the gradient at the inflection point e4 is not too large and not too small, but is an adequate gradient. Stated otherwise, at the inflection point e4, a change in the output voltage (sensitivity) with respect to a change in the air-fuel ratio is not too large and not too small. The small-gradient segment e2 that is contiguous to the inflection point e4 has a certain gradient ($\neq 0$), allowing the output voltage to be somewhat sensitive to a change in the air-fuel ratio. Generally, when the air-fuel ratio turns leaner, NOx in the exhaust gas tends to increase, and hence it is preferable to make the air-fuel ratio richer quickly. Consequently, when the air-fuel ratio turns leaner, the output voltage of the $O_2$ sensor should preferably change highly sensitively. As a result, it is preferable for the target value to be of a level substantially equal to an output voltage at the inflection point e4, i.e., to have an output voltage range in at the inflection point e4 in the vicinity of the target value.

According to the inventors' knowledge, furthermore, the output characteristics of the $O_2$ sensor change depending on the temperature of the active element thereof, as shown in FIG. 3. In FIG. 3, the solid-line curve "a", a broken-line curve "b", a dot-and-dash-line curve "c", and a two-dot-and-dash-line curve "d" represent the output characteristics of the $O_2$ sensor when the active element of the $O_2$ sensor has temperatures of 800° C., 750° C., 700° C., and 650° C., respectively. In order to explain the general output characteristics of the $O_2$ sensor as described above, the solid-line curve "a" typically has its large-gradient segment, small-gradient segment, and inflection points denoted respectively by e1 through e5 in FIG. 3. The other curves "b" through "d" which also represent the output characteristics of the $O_2$ sensor also have their large-gradient segment, small-gradient segment, and inflection points (which mean exactly the same as with the solid-line curve "a") denoted respectively by reference characters that are identical to those of the solid-line curve "a". Of each of those other curves "b" through "d", the small-gradient segment denoted by e2 refers to a small-gradient segment at richer air-fuel ratios, and the small-gradient segment denoted by e3 refers to a small-gradient segment at leaner air-fuel ratios. The inflection point denoted by e4 refers to an inflection point between the large-gradient segment e1 and the small-gradient segment e2, and the inflection point denoted by e5 refers to an inflection point between the large-gradient segment e1 and the small-gradient segment e3.

As shown in FIG. 3, the temperature of the active element of the $O_2$ sensor affects the output characteristics of the $O_2$ sensor, particularly, the gradient of the large-gradient segment e1 and the level of the output voltage in the small-gradient segment e2 at richer air-fuel ratios. Specifically, the level of the output voltage in the small-gradient segment e2 is basically lowered (and the level of the output voltage in the inflection point e4 is also lowered) as the temperature of the active element rises. More generally, the level of the output voltage in the small-gradient segment e2 changes toward the level of the output voltage in the other small-gradient segment e3 as the temperature of the active element rises. Basically, the gradient of the large-gradient segment e1 becomes more gradual as the temperature of the active element is lower. A comparison between the broken-line curve "b" which is plotted when the temperature of the active element is 750° C. and the solid-line curve "a" which is plotted when the temperature of the active element is 800° C. indicates that when the temperature of the active element of the $O_2$ sensor is 750° C. or higher, the output characteristics of the $O_2$ sensor are substantially constant i.e., changes in the output characteristics of the $O_2$ sensor with respect to changes in the temperature of the active element are small.

The inventors' knowledge also reveals that when the $O_2$ sensor with the above output characteristics is disposed downstream of a catalytic converter, e.g., a three-way catalyst, and the air-fuel ration in an exhaust gas supplied to the catalytic converter to keep the output voltage of the $O_2$ sensor at a constant value, the rates of purification by the catalytic converter of CO, HC, and NOx in the exhaust gas are correlated to the value of the output voltage of, the $O_2$ sensor, as indicated by a group of solid-line curves or a group of broken-line curves in FIG. 4 of the accompanying drawings. The group of solid-line curves in FIG. 4 shows the relationship between the rates of purification of CO, HC, and NOx and the output voltage of the $O_2$ sensor when the temperature of the active element of the $O_2$ sensor is 650° C., and the group of broken-line curves in FIG. 4 shows the relationship between the rates of purification of CO, HC, and NOx and the output voltage of the $O_2$ sensor when the temperature of the active element of the $O_2$ sensor is 800° C.

As shown in FIG. 4, the output voltage Vop of the $O_2$ sensor for optimizing the rates of purification by the catalytic converter of CO, HC, and NOx (hereinafter referred to as "purification optimizing output voltage Vop") differs depending on the temperature of the active element of the $O_2$ sensor. This is because the output characteristics of the $O_2$ sensor change depending on the temperature of the active element of the $O_2$ sensor, as described above. For example, if the temperature of the active element of the $O_2$ sensor is 650° C., then the purification optimizing output voltage Vop (650° C.) of the $O_2$ sensor is about 0.67[V], and if the temperature of the active element of the $O_2$ sensor is 800° C., then the purification optimizing output voltage Vop (800° C.) of the $O_2$ sensor is about 0.59[V].

It is to be noted in particular that the purification optimizing output voltage Vop (800° C.) of the $O_2$ sensor when the temperature of the active element of the $O_2$ sensor is 800° C. is substantially the same as the output voltage in the inflection point e4 of the output characteristics of the $O_2$ sensor (curve "a") at 800° C.. Since the output characteristics of the $O_2$ sensor are substantially constant when the temperature of the active element of the $O_2$ sensor is 750° C. or higher, as described above, the purification optimizing output voltage Vop (750° C.) (not shown) of the $O_2$ sensor when the temperature of the active element of the $O_2$ sensor is 750° C. is substantially the same as the purification optimizing output voltage Vop (800° C.) of the $O_2$ sensor at 800° C. Therefore, the purification optimizing output voltage Vop (750° C.) at 750° C. is substantially the same as the output voltage in the inflection point e4 of the curve "b".

It follows from the above analysis that (1) for controlling the air-fuel ratio in the exhaust gas to maintain the output voltage of the $O_2$ sensor at a certain target value, it is preferable for the target value and the output voltage in the inflection point e4 of the output characteristics of the $O_2$ sensor to be of substantially the same levels as each other, (2) the output characteristics of the $O_2$ sensor (particularly the levels of the output voltages in the small-gradient segment e2 and the inflection point e4) can be adjusted or kept constant by controlling the temperature of the active element of the $O_2$ sensor, and (3) when the temperature of the active element of the $O_2$ sensor which is disposed downstream of the catalytic converter is controlled at 750° C. or higher, the purification optimizing output voltage Vop of the $O_2$ sensor and the output voltage in the inflection point e4 of the output characteristics of the $O_2$ sensor are of substantially the same levels as each other.

With respect to (2) above, it is also possible to change the levels of the output voltages in the small-gradient segment e2 and the inflection point e4 by adjusting the contents of materials such as lead, silver, etc. in the active element of the $O_2$ sensor.

The present invention will be described below on the basis of the output characteristics of the $O_2$ sensor as described above. First, an $O_2$ sensor according to the present invention will be described below. In order to achieve the above object, according to the present invention, the $O_2$ sensor is used in a system for controlling an air-fuel ratio in an exhaust gas supplied from an internal combustion engine to a catalytic converter disposed in an exhaust passage of the internal combustion engine for keeping an output voltage of the $O_2$ sensor at a predetermined target value to achieve a predetermined exhaust gas purifying capability of the catalytic converter, the $O_2$ sensor being disposed in the exhaust passage downstream of the catalytic converter for generating an output voltage having a level depending on the concentration of oxygen in the exhaust gas, the output voltage changing with respect to the air-fuel ratio in the exhaust gas which is represented by the concentration of oxygen, at a gradient which switches from a large gradient to a small gradient via an inflection point as the air-fuel ratio turns richer, the $O_2$ sensor having such output characteristics that the output voltage thereof at the inflection point is substantially the same as the target value. The "inflection point" referred to above corresponds to the inflection point e4 shown in FIG. 43. For illustrative purpose, the "inflection point" which will be referred to in the description of the present invention is also denoted by "e4".

With the above arrangement of the present invention, since the target value for the output voltage of the $O_2$ sensor and the output voltage of the $O_2$ sensor at the inflection point e4 of the output characteristics thereof are substantially the same as each other, the target value is present at the inflection point. Therefore, as described above, the control properties of a process of controlling the air-fuel ratio in the exhaust gas to keep the output voltage of the $O_2$ sensor at the target value are improved. Consequently, the air-fuel ratio in the exhaust gas which is supplied from the internal combustion engine to the catalytic converter can stably be controlled at an air-fuel ratio for keeping the output voltage of the $O_2$ sensor at the target value. As a result, the catalytic converter has its required exhaust gas purifying capability maintained stably. When the output voltage of the $O_2$ sensor changes from the inflection point e4 into a leaner air-fuel ratio range due to disturbances, because the output voltage of the $O_2$ sensor shifts into the large-gradient segment, the difference between the output voltage of the $O_2$ sensor and the target value increases. As a result, the air-fuel ratio in the exhaust gas can quickly be brought back toward an air-fuel ratio corresponding to the target value. NOx contained in the exhaust gas, in particular, is thus quickly prevented from increasing.

The $O_2$ sensor according to the present invention therefore has output characteristics adequate for achieving the required exhaust gas purifying capability of the catalytic converter. The air-fuel ratio in the exhaust gas can be controlled by adjusting the amount of the fuel supplied to the internal combustion engine.

The above output characteristics of the $O_2$ sensor can be accomplished by adjusting the contents of materials that make up an active element of the $O_2$ sensor. However, the output characteristics of the $O_2$ sensor should preferably be accomplished by achieved by controlling the temperature of the active element of the $O_2$ sensor at a predetermined temperature. Preferably, the predetermined temperature is at equal to or higher than 750° C.

As the temperature of the active element of the $O_2$ sensor is kept at the predetermined temperature, the output characteristics of the $O_2$ sensor can stabilized into those characteristics which match the target value even if the temperature of the exhaust gas emitted from the internal combustion engine varies. As a result, the process of controlling the air-fuel ratio in the exhaust gas can reliably be stabilized, and hence the exhaust gas purifying capability of the catalytic converter can further be stabilized.

When the predetermined temperature is 750° C. or higher, even if the temperature of the active element of the $O_2$ sensor that is controlled varies slightly, the stability of the output characteristics of the $O_2$ sensor is high, and the target value and the average gradient of the inflection point e4 with respect to a change in the air-fuel ratio in the exhaust gas match each other well. Stated otherwise, the sensitivity of the output voltage of the $O_2$ sensor with respect to a change in the air-fuel ratio in the vicinity of the target value (=the inflection point e4) is not too high and too low, but is adequate. As a result, the control properties of the air-fuel ratio control process are effectively improved. When the temperature of the active element of the $O_2$ sensor is controlled at a temperature of 750° C. or higher, the purification optimizing output voltage Vop of the $O_2$ sensor which optimizes all of the rates of purification of CO, HC, NOx by the catalytic converter can be present at the inflection point e4. With the purification optimizing output voltage Vop set to the target value, therefore, the exhaust gas purifying capability of the catalytic converter can stably and effectively be increased in combination with the improved control properties of the air-fuel ratio control process.

The temperature of the active element of the $O_2$ sensor can be controlled by, for example, controlling energization of an electric heater combined with the $O_2$ sensor in the vicinity of the active element thereof. It is necessary to recognize the temperature of the active element of the $O_2$ sensor in order to control the temperature of the active element of the $O_2$ sensor. The temperature of the active element may be either detected directly by a temperature sensor which is coupled to the $O_2$ sensor near its active element or estimated based on a suitable model.

An apparatus for controlling an air-fuel ratio, a method of controlling an air-fuel ratio, and a recording medium which stores an air-fuel ratio control program according to the present invention will be described below. To achieve the above object, according to the present invention, there is provided an apparatus for controlling an air-fuel ratio in an exhaust gas supplied from an internal combustion engine to a catalytic converter disposed in an exhaust passage of the internal combustion engine for keeping an output voltage of an $O_2$ sensor at a predetermined target value to achieve a predetermined exhaust gas purifying capability of the catalytic converter, the $O_2$ sensor being disposed in the exhaust passage downstream of the catalytic converter for generating an output voltage having a level depending on the concentration of oxygen in the exhaust gas, the apparatus comprising sensor temperature control means for controlling the temperature of an active element of the $O_2$ sensor so as to be kept at a predetermined temperature.

According to the present invention, there is also provided a method of controlling an air-fuel ratio in an exhaust gas supplied from an internal combustion engine to a catalytic converter disposed in an exhaust passage of the internal combustion engine for keeping an output voltage of an $O_2$ sensor at a predetermined target value to achieve a predetermined exhaust gas purifying capability of the catalytic converter, the $O_2$ sensor being disposed in the exhaust passage downstream of the catalytic converter for generating an output voltage having a level depending on the concentration of oxygen in the exhaust gas, the method comprising the step of controlling the temperature of an active element of the $O_2$ sensor so as to be kept at a predetermined temperature when the air-fuel ratio in the exhaust gas is controlled.

According to the present invention, there is further provided a recording medium readable by a computer and storing an air-fuel ratio control program for enabling the computer to perform, in a system having an $O_2$ sensor disposed in an exhaust passage of an internal combustion engine downstream of a catalytic converter disposed in the exhaust passage, for generating an output voltage having a level depending on the concentration of oxygen in an exhaust gas supplied from the internal combustion engine through the exhaust passage to the catalytic converter, a process of controlling an air-fuel ratio in the exhaust gas for keeping an output voltage of the $O_2$ sensor at a predetermined target value to achieve a predetermined exhaust gas purifying capability of the catalytic converter, the air-fuel ratio control program comprising a program for enabling the computer to perform a process of controlling the temperature of an active element of the $O_2$ sensor so as to be kept at a predetermined temperature when the air-fuel ratio in the exhaust gas is controlled.

According to the present invention, since the temperature of the active element of the $O_2$ sensor is kept at the predetermined temperature, the output characteristics of the $O_2$ sensor can be kept constant. Therefore, the output characteristics of the $O_2$ sensor can be stabilized even if the temperature of the exhaust gas emitted from the internal combustion engine varies. As a result, the exhaust gas purifying capability of the catalytic converter can be stabilized by the process of controlling the air-fuel ratio in the exhaust gas to maintain the output voltage of the $O_2$ sensor at the predetermined target value.

According to the present invention (the apparatus for controlling the air-fuel ratio, the method of controlling the air-fuel ratio, and the recording medium which stores the air-fuel ratio control program), the predetermined temperature is preferably equal to or higher than 750° C. With the above predetermined temperature, the output characteristics of the $O_2$ sensor can stabilized even if the temperature of the active element of the $O_2$ sensor which is controlled varies slightly. As a result, the exhaust gas purifying capability of the catalytic converter can be stabilized. The $O_2$ sensor generally comprises a sensor for generating an output voltage which changes with respect to the air-fuel ratio in the exhaust gas which is represented by the concentration of oxygen, at a gradient which switches from a large gradient to a small gradient via an inflection point e4 as the air-fuel ratio turns richer. When the temperature of the active element of the $O_2$ sensor is controlled at a temperature of 750° C. or higher, the purification optimizing output voltage Vop of the $O_2$ sensor which optimizes all of the rates of purification of CO, HC, NOx by the catalytic converter can be present at the inflection point e4. With the purification optimizing output voltage Vop set to the target value, therefore, the exhaust gas purifying capability of the catalytic converter can stably and effectively be increased in combination with the improved control properties of the air-fuel ratio control process.

According to the present invention (the apparatus for controlling the air-fuel ratio, the method of controlling the air-fuel ratio, and the recording medium which stores the air-fuel ratio control program), if the $O_2$ sensor comprises a sensor for generating an output voltage which changes with respect to the air-fuel ratio in the exhaust gas which is represented by the concentration of oxygen, at a gradient which switches from a large gradient to a small gradient via an inflection point as the air-fuel ratio turns richer, then the predetermined temperature is preferably a temperature which is determined such that the output voltage of the $O_2$ sensor at the inflection point is substantially the same as the target value when the temperature of the active element of the $O_2$ sensor is kept at the temperature.

By thus controlling the temperature of the active element of the $O_2$ sensor, the target value for the output voltage of the $O_2$ sensor and the output voltage at the inflection point e4 are substantially the same as each other, so that the target value is present at the inflection point e4. As described above with respect to the $O_2$ sensor according to the present invention, therefore, the control properties of a process of controlling the air-fuel ratio in the exhaust gas to keep the output voltage of the $O_2$ sensor at the target value are improved. Consequently, the air-fuel ratio in the exhaust gas which is supplied from the internal combustion engine to the catalytic converter can stably be controlled at an air-fuel ratio for keeping the output voltage of the $O_2$ sensor at the target value. As a result, the catalytic converter has its required exhaust gas purifying capability maintained effectively and stably. When the output voltage of the $O_2$ sensor changes from the inflection point e4 into a leaner air-fuel ratio range due to disturbances, the air-fuel ratio in the exhaust gas can quickly be brought back toward an air-fuel ratio corresponding to the target value. NOx contained in the exhaust gas, in particular, is thus quickly prevented from increasing.

In the apparatus for controlling the air-fuel ratio according to the present invention, the sensor temperature control means should preferably control the temperature of the $O_2$ sensor at a temperature lower than the predetermined temperature until a predetermined period of time elapses after the internal combustion engine has started. Similarly, the method of controlling the air-fuel ratio according to the present invention should preferably have the step of controlling the temperature of the $O_2$ sensor at a temperature lower than the predetermined temperature until a predetermined period of time elapses after the internal combustion engine has started. Likewise, in the recording medium storing the air-fuel ratio control program, the air-fuel ratio control program should preferably comprise a program for enabling the computer to perform a process of controlling the temperature of the $O_2$ sensor at a temperature lower than the predetermined temperature until a predetermined period of time elapses after the internal combustion engine has started. The temperature lower than the predetermined temperature is 600° C., for example.

With the above arrangement, even if moisture in the exhaust gas is deposited on the active element of the $O_2$ sensor, the active element is prevented from being abruptly heated and hence from being damaged due to thermal stress or the like.

In the apparatus for controlling the air-fuel ratio according to the present invention, if the sensor temperature control means controls the temperature of the active element of the $O_2$ sensor with an electric heater, then the sensor temperature control means should preferably de-energize the electric heater when the temperature of the electric heater is in excess of a predetermined upper limit (e.g., 930° C.). Similarly, in the method of controlling the air-fuel ratio according to the present invention, if the temperature of the active element of the $O_2$ sensor can be controlled by an electric heater, then the method should preferably comprise the step of de-energizing the electric heater when the temperature of the electric heater is in excess of a predetermined upper limit. Likewise, in the recording medium storing the air-fuel ratio control program according to the present invention, if the temperature of the active element of the $O_2$ sensor can be controlled by an electric heater, then the air-fuel ratio control program should preferably comprise a program for enabling the computer to perform a process of de-energizing the electric heater when the temperature of the electric heater is in excess of a predetermined upper limit.

With the electric heater thus controlled in its energization, it is possible to prevent the electric heater from suffering a disconnection and also to prevent the active element of the $O_2$ sensor which incorporates the electric heater from being damaged by overheating.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

Figure 1:
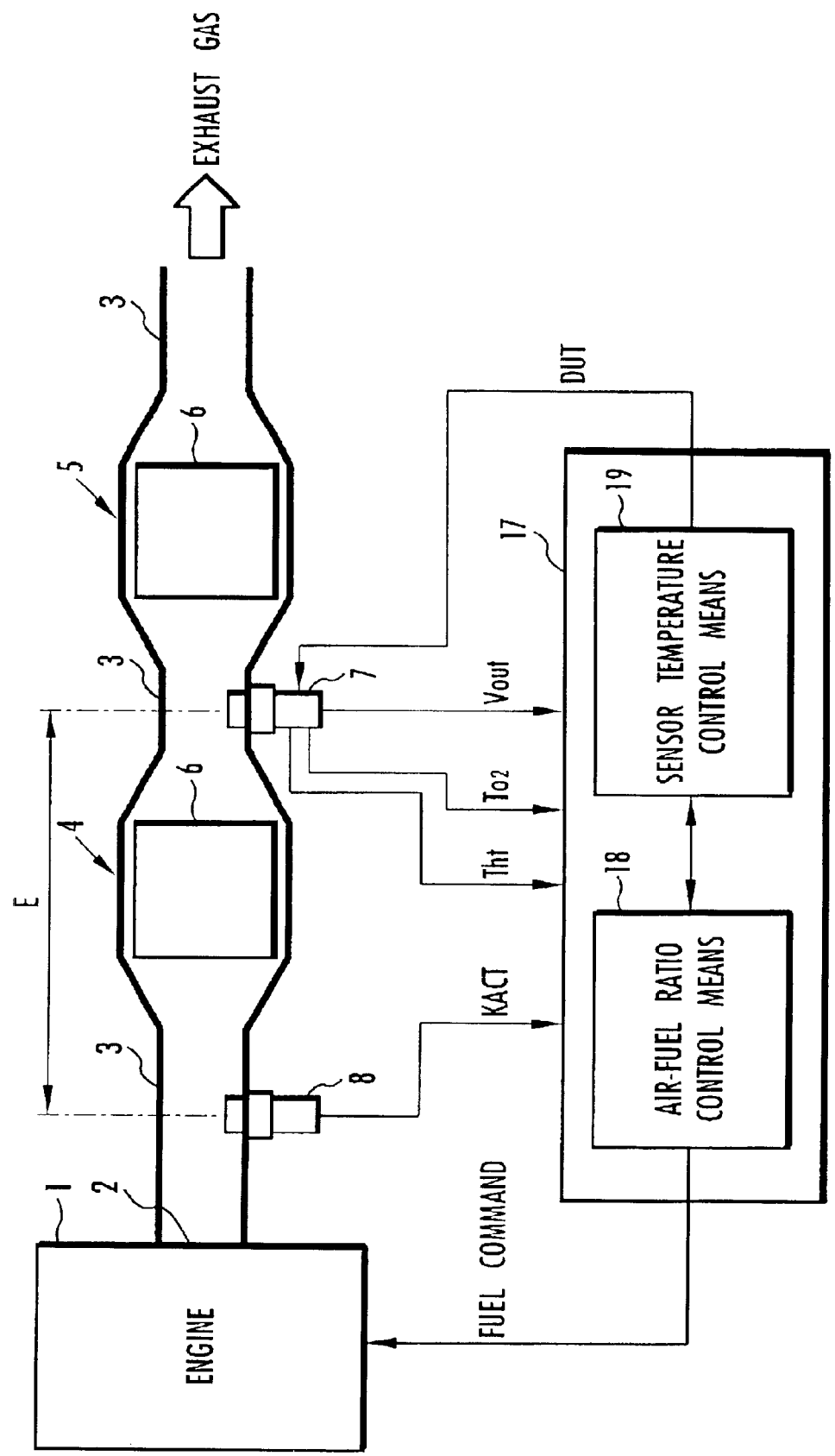
FIG. 1 is a block diagram of an air-fuel ratio control apparatus according to a first embodiment of the present invention.
Figure 2:
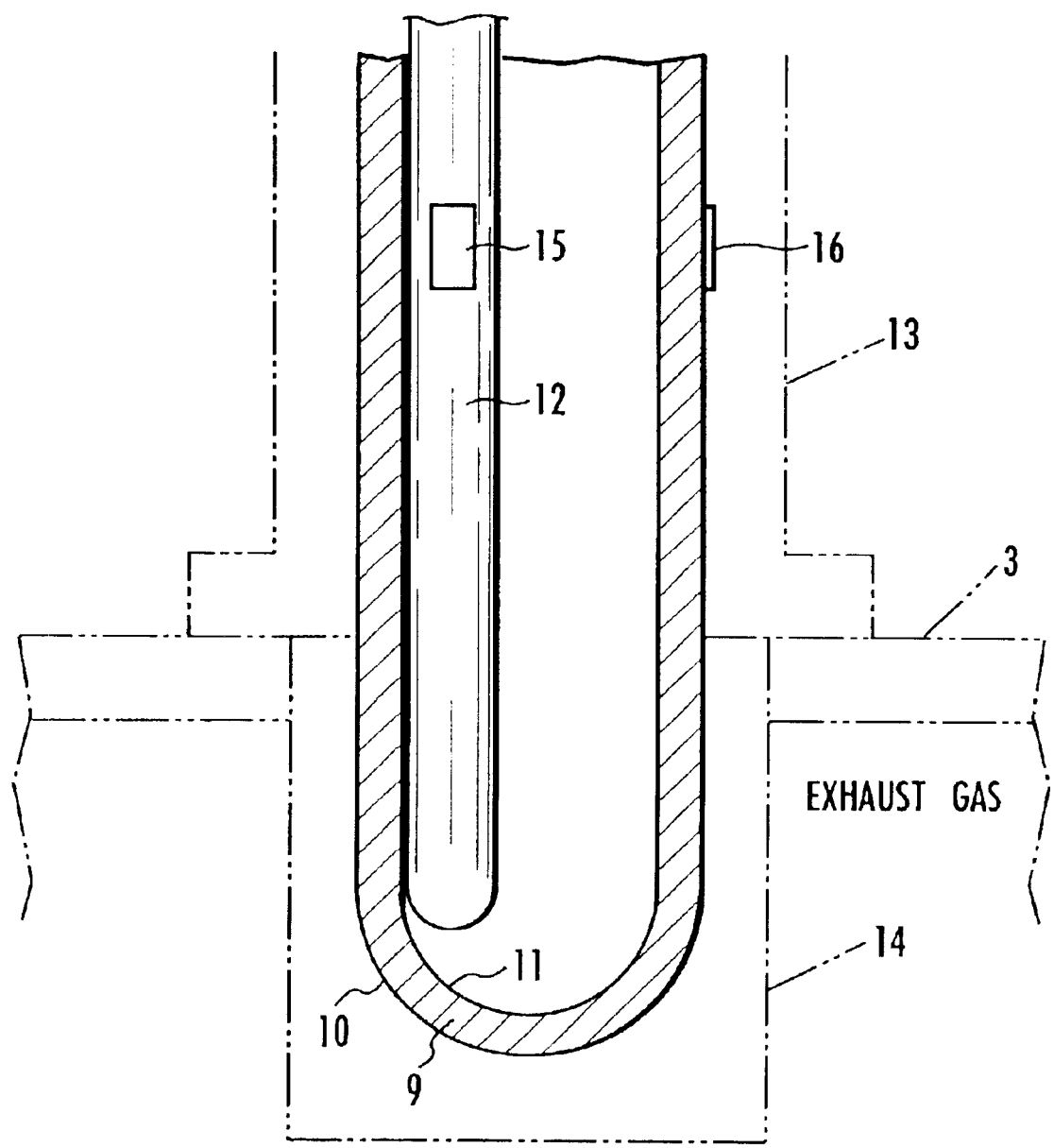
FIG. 2 is a fragmentary cross-sectional view of an $O_2$ sensor in the air-fuel ratio control apparatus shown in FIG. 2.
Figure 3:
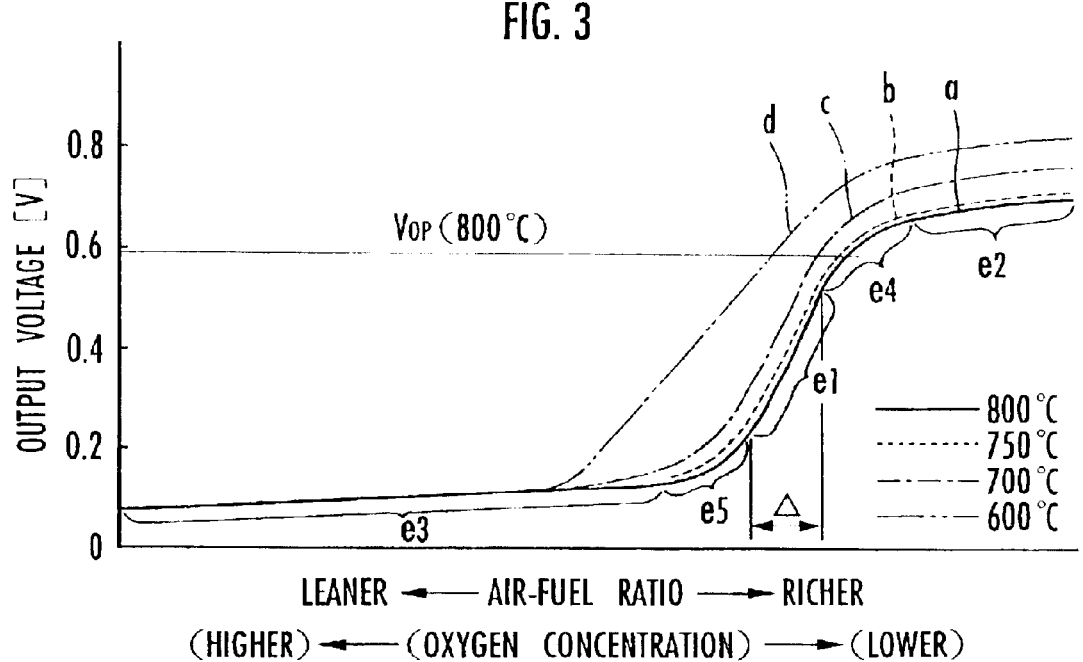
FIG. 3 is a diagram showing output characteristics of an $O_2$ sensor.

A first embodiment of the present invention will be described below with reference to FIGS. 1 and 2 and also FIGS. 3 and 4 described above. FIG. 1 shows in block form an air-fuel ratio control apparatus according to a first embodiment of the present invention. In FIG. 1, an engine (an internal combustion engine) 1 mounted on an automobile, a hybrid vehicle, or the like combusts a mixture of fuel and air and generates an exhaust gas, which is discharged into the atmosphere through an exhaust pipe 3 (an exhaust passage) extending from an exhaust port 2 of the engine 1. The exhaust pipe 3 incorporates therein two catalytic converters 4, 5 disposed successively downstream for purifying the exhaust gas emitted from the engine 1 and flowing through the exhaust pipe 3. Each of the catalytic converters 4, 5 contains a three-way catalyst 6, for example. Though the catalytic converters 4, 5 are shown as being separate from each other in FIG. 1, they may be of a unitary structure with two catalytic beds, each comprising a three-way catalyst, disposed respectively in upstream and downstream regions thereof.

In the present embodiment, the air-fuel ratio in the exhaust gas emitted from the engine 1 is controlled in order for the upstream catalytic converter 4 to have a good exhaust gas purifying capability (the ability of the catalytic converter 4 to purify CO, HC, and NOx). For controlling the air-fuel ratio in the exhaust gas, an $O_2$ sensor 7 is mounted on the exhaust pipe 3 downstream of the catalytic converter 4 and upstream of the catalytic converter 5, and a wide-range air-fuel ratio sensor 8 is mounted on the exhaust pipe 3 upstream of the catalytic converter 4. The $O_2$ sensor 7, whose structural details will be described later on, comprises an $O_2$ sensor for generating an output voltage Vout according to the characteristics shown in FIG. 3 with respect to the air-fuel ratio in the exhaust gas which has passed through the catalytic converter 4 and which is brought into contact with an active element (a sensitive element) of the $O_2$ sensor 7. The wide-range air-fuel ratio sensor 8 comprises a sensor for generating an output voltage which is in proportion to the air-fuel ratio in the exhaust gas which-is to enter the catalytic converter 4 and which is brought into contact with an active element (sensitive element) of the wide-range air-fuel ratio sensor 8. The wide-range air-fuel ratio sensor 8 is the same as the air-fuel ratio sensor disclosed in Japanese laid-open patent publication No. 4-36947by the applicant of the present application, and generates an output voltage KACT proportional to the air-fuel ratio in the exhaust gas. The wide-range air-fuel ratio sensor will hereinafter be referred to as "LAF sensor".

The $O_2$ sensor 7 will be described in detail below. The $O_2$ sensor 7 is of a structure as shown in FIG. 2. As shown in FIG. 2, the $O_2$ sensor 7 has an active element 9 in the form of a hollow bottomed cylinder made primarily of a solid electrolyte permeable to oxygen ions, e.g., stabilized zirconia ($ZrO_2+Y_2O_3$). The active element 9 has outer and inner surfaces coated with porous platinum electrodes 10, 11, respectively. The $O_2$ sensor 7 also has a rod-shaped ceramic heater 12 inserted as an electric heater into the active element 9 for heating the active element 9 for activation and controlling the temperature of the active element 9. The active element 9 is filled with air containing oxygen at a constant concentration, i.e., under a constant partial pressure, in a space around the ceramic heater 12. The $O_2$ sensor 7 is placed in a sensor casing 13 mounted on the exhaust pipe 3 such that the tip end of the active element 9 has its outer surface positioned in contact with the exhaust gas flowing in the exhaust pipe 3. The tip end of the active element 9 is covered with a tubular protector 14 which protects the active element 9 against the impingement of foreign matter thereon. The tip end of the active element 9 which is positioned in the exhaust pipe 3 contacts the exhaust gas through a plurality of holes (not shown) defined in the protector 14.

The $O_2$ sensor 7 thus constructed operates as follows: An electromotive force depending on the concentration of oxygen in the exhaust gas is generated between the platinum electrodes 10, 11 based on the difference between the concentration of oxygen in the exhaust gas which is brought into contact with the outer surface of the tip end of the active element 9 and the concentration of oxygen in the air in the active element 9. The generated electromotive force is amplified by an amplifier (not shown), and then produced as the output voltage Vout from the $O_2$ sensor 7.

In the present embodiment, temperature sensors 15, 16, each comprising a thermocouple, are mounted respectively on the ceramic heater 12 and the active element 9 for detecting respective temperatures of the ceramic heater 12 and the active element 9. The temperature sensor 15 produces an output voltage Tht depending on the temperature of the ceramic heater 12 and outputs the output voltage Tht through an amplifier (not shown). The temperature sensor 16 produces an output voltage To2 depending on the temperature of the active element 9 and outputs the output voltage To2 through an amplifier (not shown).

As shown in FIG. 1, the air-fuel ratio control apparatus also has a control unit 17 comprising a microcomputer. The control unit 17 is supplied with the output voltage KACT from the LAF sensor 8, the output voltage Vout from the $O_2$ sensor 7, and the output voltages To2, Tht from the temperature sensors 15, 16. The control unit 17 has an air-fuel ratio control means 18 and a sensor temperature control means 19 as its functional means. The air-fuel ratio control means 18 controls the air-fuel ratio in the exhaust gas to settle and keep the output voltage Vout from the $O_2$ sensor 7 at a predetermined target value Vop (a constant value), using the output voltage KACT from the LAF sensor 8 and the output voltage Vout from the $O_2$ sensor 7.

More specifically, the air-fuel ratio control means 18 controls the air-fuel ratio in the exhaust gas as described in paragraphs [0071]-[0362] in the specification of Japanese laid-open patent publication No. 11-324767or column 9, line 39 through column 44, line 39 of U.S. Pat. No. 6,188,953, for example. The air-fuel ratio control process performed by the air-fuel ratio control means 18 is summarized as follows: The air-fuel ratio control means 18 regards an exhaust system E ranging from the LAF sensor 8 to the $O_2$ sensor 7 and including the catalytic converter 4, of the entire exhaust system of the engine 1, as an object to be controlled which is supplied with output voltage KACT from the LAF sensor 8 as an input and produces the output voltage Vout from the $O_2$ sensor 7 as an output. The air-fuel ratio control means 18 sequentially determines, according to an adaptive sliding mode control process, a target air-fuel ratio (a target air-fuel ratio for the air-fuel ratio in the exhaust gas detected by the LAF sensor 8) which serves as a target input for the exhaust system E that is required to converge the output voltage Vout from the $O_2$ sensor 7 as the output of the exhaust system E to the target value Vout. Then, the air-fuel ratio control means 18 generates a fuel command for adjusting the amount of the fuel to be supplied to the engine 1 (and hence the air-fuel ratio of the air-fuel mixture to be combusted in the engine 1) according to an adaptive control process or a PID control process in order to converge the air-fuel ratio in the exhaust gas detected by the LAF sensor 8 to the target air-fuel ratio. The amount of the fuel to be supplied to the engine 1 is now adjusted according to the fuel command.

In order to calculate the target air-fuel ratio, for compensating for the effect of a dead time that is present between the output voltage KACT of the LAF sensor 8 (the input of the exhaust system E) and the output voltage Vout (the output of the exhaust system E) of the $O_2$ sensor 7, and a dead time that is present between the target air-fuel ratio and the air-fuel ratio in the exhaust gas detected by the LAF sensor 8, the air-fuel ratio control means 18 compensates sequentially determines an estimated value for the output voltage Vout of the $O_2$ sensor 7 after the sum of the above dead times. The air-fuel ratio control means 18 then calculates the target air-fuel ratio according to the adaptive sliding mode control process so as to converge the estimated value to the target value Vop (and as a result to converge the output voltage Vout of the $O_2$ sensor 7 to the target value Vop). In order to compensate for the effect of dynamic characteristic changes of the exhaust system E, furthermore, the air-fuel ratio control means 18 sequentially identifies the parameters of a model of the exhaust system E which is used to perform the adaptive sliding mode control process and calculate the estimate value for the output voltage Vout of the $O_2$ sensor 7 after the sum of the dead times.

Figure 4:
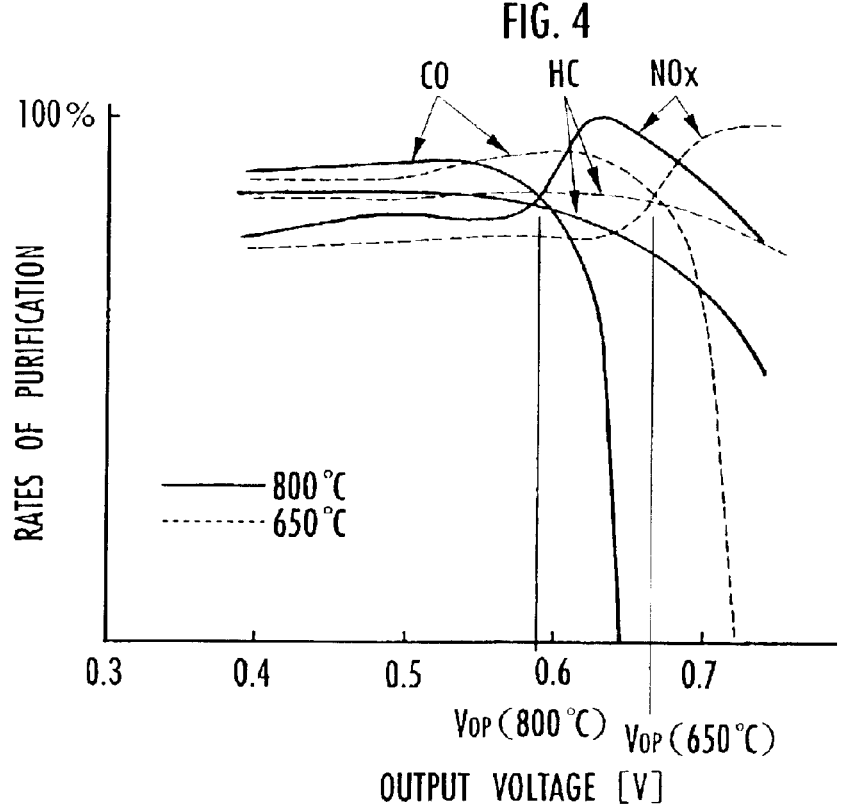
FIG. 4 is a diagram showing the relationship between the output voltage of an $O_2$ sensor disposed downstream of a catalytic converter and the rates of purification by the catalytic converter of exhaust gas components.

In the present embodiment, the target value Vop for the output voltage Vout of the $O_2$ sensor 7 is such a value as to optimize the rates of purification by the catalytic converter of CO, HC, and NOx in the exhaust gas when the temperature of an active element of the $O_2$ sensor is 800° C., for example, i.e., a value Vop(800° C.) shown in FIG. 4.

The sensor temperature control means 19 basically energizes of the ceramic heater 12 in order to equalize the temperature of the active element 9 which is represented by the output voltage To2 of the temperature sensor 16 coupled to the $O_2$ sensor 7 to the temperature (800° C.) of the active element 9 which corresponds to the target value Vop for the output voltage Vout of the $O_2$ sensor 7 in the present embodiment. At this time, the ceramic heater 12 is energized by a pulsed voltage. Specifically, the sensor temperature control means 19 adjusts the duty cycle DUT of the pulsed voltage to adjust the amount of electric energy supplied to the ceramic heater 12 and hence the amount of heat generated by the ceramic heater 12. The sensor temperature control means 19 sequentially determines the duty cycle DUT of the pulsed voltage according to a feedback control process (e.g., a PID control process) in order to converge the temperature of the active element 9 which is represented by the output voltage To2 of the temperature sensor 16 coupled to the $O_2$ sensor 7 to the target value of 800° C., and energizes the ceramic heater 12 under the pulsed voltage with the determined duty cycle DUT.

The control unit 17 incorporates there, as a recording medium according to the present invention, a ROM (not shown) which stores a program for enabling the microcomputer to perform the processing sequences of the air-fuel ratio control means 18 and the sensor temperature control means 19.

Overall operation of the air-fuel ratio control apparatus according to the present embodiment will be described below. The air-fuel ratio control means 18 of the control unit 17 controls the air-fuel ratio in the exhaust gas to keep the output voltage Vout of the $O_2$ sensor 7 at the target value Vop (800° C.) as described above while the engine 1 is in operation (after the LAF sensor 8 and the $O_2$ sensor 7 are activated). Concurrent with the operation of the air-fuel ratio control means 18, the sensor temperature control means 19 energizes the-ceramic heater 12 to converge the temperature of the active element 9 which is represented by the output voltage To2 of the temperature sensor 16 to the target value of 800° C.

When the ceramic heater 12 is thus energized, the temperature of the active element 9 is kept at 800° C. Therefore, the $O_2$ sensor 7 has its output characteristics indicated by the solid-line curve "a" in FIG. 3, and the target value Vop (800°

C.) for the output voltage Vout of the $O_2$ sensor 7 is steadily present at the inflection point e4. Accordingly, a change (sensitivity) in the output voltage Vout of the $O_2$ sensor 7 with respect to a change in the air-fuel ratio in the exhaust gas in the vicinity of the target value Vop (800° C.) is too large and not too small, but is adequate. Therefore, the air-fuel ratio control means 18 can control the air-fuel ratio in the exhaust gas in order to be able to keep the output voltage Vout of the $O_2$ sensor 7 at the target value Vop (800° C.) stably with high accuracy. As a result, the exhaust gas purifying capability of the catalytic converter 4 can be maintained reliably and stably in an optimum state.

If the air-fuel ratio in the exhaust gas turns leaner while the output voltage Vout of the $O_2$ sensor 7 is kept close to the target value Vop (800° C.), then NOx contained in the exhaust gas tends to increase. When the air-fuel ratio in the exhaust gas turns leaner, however, since the output voltage Vout changes largely toward the large-gradient segment e1 (see FIG. 3) of the output characteristics of the $O_2$ sensor 7, the air-fuel ratio in the exhaust gas is controlled by the air-fuel ratio control means 18 to bring the output voltage Vout quickly back toward the target value Vop (800° C.). Thus, the increase in NOx contained in the exhaust gas can quickly be suppressed.

In the present embodiment, the sensor temperature control means 19 carries out the following temperature control process in addition to the energization of the ceramic heater 12: When the exhaust pipe and the $O_2$ sensor 7 are cold and then the $O_2$ sensor 7 is abruptly heated as when the engine 1 is started from a cold state, the active element 9 of the $O_2$ sensor 7 may possibly be damaged under thermal stress due to moisture in the exhaust gas which has been deposited on the active element 9. According to the present embodiment, the sensor temperature control means 19 energizes the ceramic heater 12 with the target value for the temperature of the active element 9 being set to a temperature lower than 800° C., e.g., 600° C., until a predetermined period of times elapses after the start of the engine 1, i.e., until a period of time in which the active element 9 is heated to a temperature to evaporate moisture deposited thereon elapses. This temperature control process is effective to prevent the active element 9 from being heated abruptly and hence to prevent the active element 9 from being damaged after the engine 1 has started. The target value for the temperature of the active element 9 in this temperature control process is preferably about 600° C. in order to quickly activate the active element 9 while preventing the active element 9 from being damaged.

If the temperature of the ceramic heater 12 is excessively high, then the ceramic heater 12 may possibly suffer a disconnection. According to the present embodiment, the sensor temperature control means 19 de-energizes the ceramic heater 12 when the temperature of the ceramic heater 12 which is represented by the output voltage Tht of the temperature sensor 15 rises to a predetermined upper limit (e.g., 930° C.). In this manner, the ceramic heater 12 is prevented from suffering an undesirable disconnection when it is energized.

A second embodiment of the present invention will be described below. In the first embodiment, the temperature of the active element 9 of the $O_2$ sensor 7 is detected by the temperature sensor 16. According to the second embodiment, the temperature of the active element 9 of the $O_2$ sensor 7 is estimated rather than being detected by a temperature sensor.

An estimated value To2_hat for the temperature of the active element 9 is normally in substantial agreement, with a time lag of first order, with the temperature of the exhaust gas that is introduced from the exhaust port 2 of the engine 1 into the exhaust pipe 3, and is sequentially calculated according to the following equation (1), for example:

$$To2\_hat(k)=(1-Ktex)\cdot To2\_hat(k-1) + Ktex\cdot Texg\_MAP(NE(k), PB(k)) \quad (1)$$

where k represents the kth control cycle of the sensor temperature control means 19, Texg_MAP(NE(k), PB(k)) represents the temperature determined as the temperature of the exhaust gas from the engine 1 from a preset map based on the rotational speed NE of the engine 1 and the intake pressure (the absolute pressure in the intake pipe of the engine 1) PB, and Ktex represents a predetermined constant. An initial value of the estimated value To2_hat for the temperature of the active element 9 is determined from a data table or the like based on the temperature of the engine 1 at the time it is started.

The sensor temperature control means 19 sequentially determines a duty cycle DUT of the pulsed voltage to be applied to the ceramic heater 12 in order to converge the estimated value To2_hat for the temperature of the active element 9, which is determined according to the above equation (1) in each control cycle, to the target value 800° C. (the target value is 600° C. in a predetermined period of time after the start of the engine 1), and then energizes the ceramic heater 12 under the pulsed voltage with the determined duty cycle DUT. In the second embodiment, therefore, the estimated value To2_hat is used instead of the output voltage To2 the detected value of the temperature of the active element 9) of the temperature sensor 16 which is used to control the energization of the ceramic heater 12 in the first embodiment.

The second embodiment as described above can offer the same advantages as the first embodiment. According to the second embodiment, the cost of the air-fuel ratio control apparatus is reduced because the temperature sensor 16 for detecting the temperature of the active element 9 is dispensed with.

Although certain preferred embodiments of the present invention have been shown and described in detail, it should be understood that various changes and modifications may be made therein without departing from the scope of the appended claims.

What is claimed is:

1. An $O_2$ sensor in a system for controlling an air-fuel ratio in an exhaust gas supplied from an internal combustion engine to a catalytic converter disposed in an exhaust passage of the internal combustion engine for keeping an output voltage of the $O_2$ sensor at a predetermined target value to achieve a predetermined exhaust gas purifying capability of the catalytic converter, said $O_2$ sensor being disposed in the exhaust passage downstream of said catalytic converter for generating an output voltage having a level depending on the concentration of oxygen in the exhaust gas, said output voltage changing with respect to the air-fuel ratio in the exhaust gas which is represented by the concentration of oxygen, at a gradient which switches from a large gradient to a small gradient via an inflection point as said air-fuel ratio turns richer, said $O_2$ sensor having such output characteristics that the output voltage thereof at said inflection point is substantially the same as said target value.

2. An $O_2$ sensor according to claim 1, wherein said output characteristics of said $O_2$ sensor are achieved by controlling the temperature of an active element of the $O_2$ sensor at a predetermined temperature.

3. An $O_2$ sensor according to claim 2, wherein said predetermined temperature is equal to or higher than 750° C.

4. An apparatus for controlling an air-fuel ratio in an exhaust gas supplied from an internal combustion engine to a catalytic converter disposed in an exhaust passage of the internal combustion engine for keeping an output voltage of an $O_2$ sensor at a predetermined target value to achieve a predetermined exhaust gas purifying capability of the catalytic converter, said $O_2$ sensor being disposed in the exhaust passage downstream of said catalytic converter for generating an output voltage having a level depending on the concentration of oxygen in the exhaust gas, said apparatus comprising:

sensor temperature control means for controlling the temperature of an active element of the $O_2$ sensor responsive to the temperature of the exhaust gas so as to be kept at a predetermined temperature.

5. An apparatus according to claim 4, wherein said predetermined temperature is equal to or higher than 750° C.

6. An apparatus according to claim 4 or 5, wherein said $O_2$ sensor comprises a sensor for generating an output voltage which changes with respect to the air-fuel ratio in the exhaust gas which is represented by the concentration of oxygen, at a gradient which switches from a large gradient to a small gradient via an inflection point as said air-fuel ratio turns richer, said predetermined temperature being a temperature which is determined such that the output voltage of said $O_2$ sensor at said inflection point is substantially the same as said target value when the temperature of the active element of the $O_2$ sensor is kept at said temperature.

7. An apparatus according to claim 4, wherein said sensor temperature control means comprises controlling means for controlling the temperature of said $O_2$ sensor at a temperature lower than said predetermined temperature until a pre-determined period of time elapses after said internal combustion engine has started.

8. An apparatus according to claim 4, wherein said sensor temperature control means comprises controlling means for controlling the temperature of the active element of the $O_2$ sensor with an electric heater, and de-energizing said electric heater when the temperature of said electric heater is in excess of a predetermined upper limit.

9. A method of controlling an air-fuel ratio in an exhaust gas supplied from an internal combustion engine to a catalytic converter disposed in an exhaust passage of the internal combustion engine for keeping an output voltage of an $O_2$ sensor at a predetermined target value to achieve a predetermined exhaust gas purifying capability of the catalytic converter, said $O_2$ sensor being disposed in the exhaust passage downstream of said catalytic converter for generating an output voltage having a level depending on the concentration of oxygen in the exhaust gas, said method comprising the step of:

controlling the temperature of an active element of the $O_2$ sensor responsive to the temperature of the exhaust gas so as to be kept at a predetermined temperature when the air-fuel ratio in the exhaust gas is controlled.

10. A method according to claim 9, wherein said predetermined temperature is equal to or higher than 750° C.

11. A method according to claim 9, wherein said $O_2$ sensor comprises a sensor for generating an output voltage which changes with respect to the air-fuel ratio in the exhaust gas which is represented by the concentration of oxygen, at a gradient which switches from a large gradient to a small gradient via an inflection point as said air-fuel ratio turns richer, said predetermined temperature being a temperature which is determined such that the output voltage of said $O_2$ sensor at said inflection point is substantially the same as said target value when the temperature of the active element of the $O_2$ sensor is kept at said temperature.

12. A method according to claim 9, further comprising the step of controlling the temperature of said $O_2$ sensor at a temperature lower than said predetermined temperature until a predetermined period of time elapses after said internal combustion engine has started.

13. A method according to claim 9, wherein the temperature of the active element of the $O_2$ sensor can be controlled by an electric heater, further comprising the step of de-energizing said electric heater when the temperature of said electric heater is in excess of a predetermined upper limit.

14. A recording medium readable by a computer and storing an air-fuel ratio control program for enabling said computer to perform, in a system having an $O_2$ sensor disposed in an exhaust passage of an internal combustion engine downstream of a catalytic converter disposed in said exhaust passage, for generating an output voltage having a level depending on the concentration of oxygen in an exhaust gas supplied from said internal combustion engine through said exhaust passage to said catalytic converter, a process of controlling an air-fuel ratio in the exhaust gas for keeping an output voltage of the $O_2$ sensor at a predetermined target value to achieve a predetermined exhaust gas purifying capability of the catalytic converter, said air-fuel ratio control program comprising a program for enabling said computer to perform a process of controlling the temperature of an active element of the $O_2$ sensor responsive to the temperature of the exhaust gas so as to be kept at a predetermined temperature when the air-fuel ratio in the exhaust gas is controlled.

15. A recording medium according to claim 14, wherein said predetermined temperature is equal to or higher than 750° C.

16. A recording medium according to claim 14, wherein said $O_2$ sensor comprises a sensor for generating an output voltage which changes with respect to the air-fuel ratio in the exhaust gas which is represented by the concentration of oxygen, at a gradient which switches from a large gradient to a small gradient via an inflection point as said air-fuel ratio turns richer, said predetermined temperature being a temperature which is determined such that the output voltage of said $O_2$ sensor at said inflection point is substantially the same as said target value when the temperature of the active element of the $O_2$ sensor is kept at said temperature.

17. A recording medium according to claim 14, wherein said air-fuel ratio control program comprises a program for enabling said computer to perform a process of controlling the temperature of said $O_2$ sensor at a temperature lower than said predetermined temperature until a predetermined period of time elapses after said internal combustion engine has started.

18. A recording medium according to claim 14, wherein the temperature of the active element of the $O_2$ sensor can be controlled by an electric heater, said air-fuel ratio control program comprising a program for enabling said computer to perform a process of de-energizing said electric heater when the temperature of said electric heater is in excess of a predetermined upper limit.

* * * * *